100
United States Patent [19]

Fussell

[11] Patent Number: 4,554,927
[45] Date of Patent: Nov. 26, 1985

[54] PRESSURE AND TEMPERATURE SENSOR

[75] Inventor: Theodore J. Fussell, Bridgewater, N.J.

[73] Assignee: Thermometrics Inc., Edison, N.J.

[21] Appl. No.: 527,742

[22] Filed: Aug. 30, 1983

[51] Int. Cl.[4] .............................................. A61B 5/02
[52] U.S. Cl. ...................................... 128/670; 73/714; 73/727; 374/143; 128/673
[58] Field of Search ............... 128/670, 673, 675, 736, 128/748; 73/710, 719, 721, 725, 727, 753, 754; 374/143, 178, 185

[56] References Cited

U.S. PATENT DOCUMENTS

| | | | |
|---|---|---|---|
| 2,081,405 | 5/1937 | Mason | 178/44 |
| 3,088,323 | 5/1963 | Welkowitz et al. | 73/398 |
| 3,245,264 | 4/1966 | Kaplan et al. | 73/398 |
| 3,550,583 | 12/1970 | Chiku | 128/2.05 |
| 3,553,625 | 1/1971 | Stedman | 128/675 X |
| 3,572,322 | 3/1971 | Wade | 128/670 X |
| 3,683,213 | 8/1972 | Staudte | 310/9.6 |
| 3,710,781 | 1/1973 | Huthcins, IV et al. | 128/2.05 D |
| 3,724,274 | 4/1973 | Millar | 73/398 AR |
| 3,745,385 | 7/1973 | Nakajima et al. | 310/9.5 |
| 3,748,623 | 7/1973 | Millar | 338/4 |
| 3,880,151 | 4/1975 | Nilsson et al. | 128/673 |
| 3,916,877 | 11/1975 | Bechman | 128/670 |
| 3,968,466 | 7/1976 | Nakamura et al. | 338/42 |
| 4,003,370 | 1/1977 | Emil et al. | 128/673 |
| 4,023,562 | 5/1977 | Hynecek et al. | 128/2.05 |
| 4,085,620 | 4/1978 | Tanaka | 73/727 |
| 4,166,269 | 8/1979 | Stephens et al. | 338/3 |
| 4,191,193 | 3/1980 | Seo | 73/727 X |
| 4,222,277 | 9/1980 | Kurtz et al. | 73/721 |
| 4,262,532 | 4/1981 | Butler et al. | 374/143 |
| 4,274,423 | 6/1981 | Mizuno et al. | 128/675 |
| 4,300,395 | 11/1981 | Shirovzu et al. | 73/727 X |
| 4,320,664 | 3/1982 | Rehn et al. | 73/727 X |
| 4,327,350 | 4/1982 | Erichsen | 338/4 |
| 4,342,231 | 8/1982 | Yamamoto et al. | 73/721 |
| 4,357,834 | 11/1982 | Kimura | 73/708 |
| 4,366,714 | 1/1983 | Aaorni | 73/753 |

FOREIGN PATENT DOCUMENTS 691690 10/1979 U.S.S.R. .............................. 374/143

Primary Examiner—Edward M. Coven
Attorney, Agent, or Firm—Lerner, David, Littenberg, Krumholz & Mentlik

[57] ABSTRACT

A gauge element for and a pressure sensor for sensing phenomena such as pressure and temperature comprising a substantially U-shaped unitary piezoresistive element formed from a silicon crystal. When employed for sensing pressure and temperature, resistor means are provided along with means for coupling the first and second legs of the piezoresistive element in an electrical circuit to provide a temperature independent output indicative of the pressure imparted to one leg of the piezoresistive element, and for coupling the second leg and the resistor means to provide an output independent of the pressure imparted to the first leg and indicative of the environmental temperature. This configuration is particularly suitable for miniaturization and therefore useful for biomedical applications wherein the sensor can be inserted into a body transcutaneously by a catheter.

15 Claims, 5 Drawing Figures

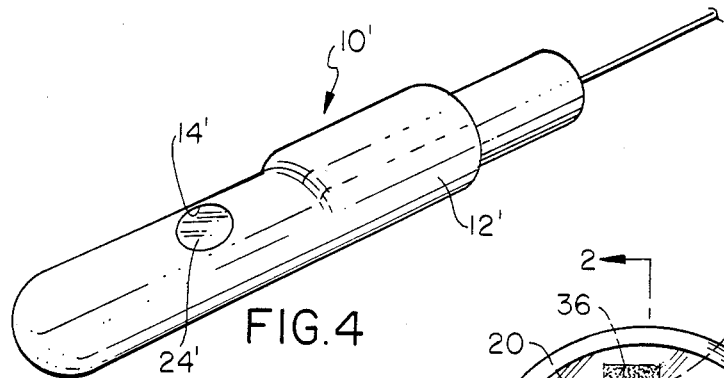
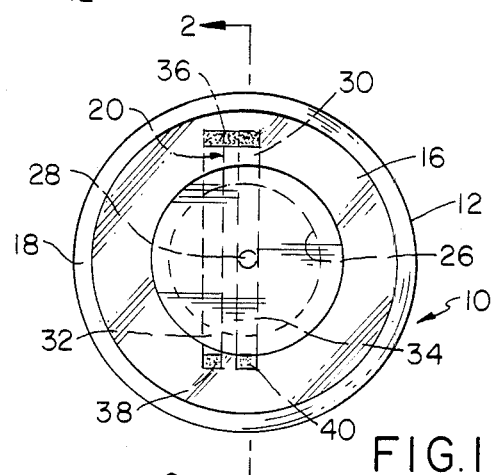
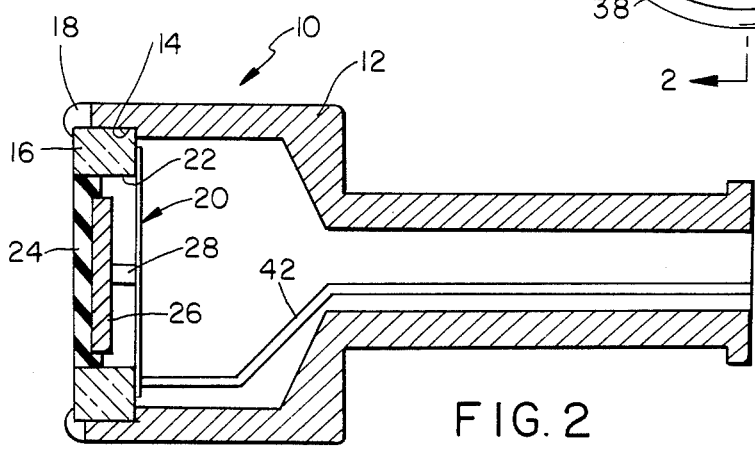
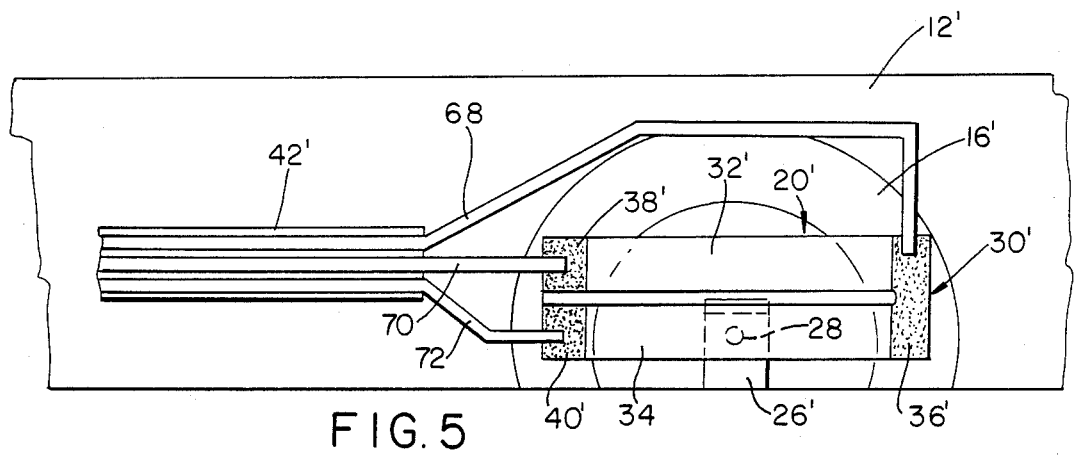

PRESSURE AND TEMPERATURE SENSOR

BACKGROUND OF THE INVENTION

1. Field of the Invention

The present invention relates to pressure sensors, and more particularly to pressure sensors which compensate for temperature variations and which can provide absolute temperature readings for use, inter alia, in biomedical applications.

2. Description of the Prior Art

In the field of physiological pressure measurement transducers and particularly as to miniature intra corporeal blood pressure measuring transducers, there presently are two kinds of transducers used for internal blood measurements in biological bodies. The most commonly used is the extra corporeal type wherein a lumen in a physiological catheter conducts pressure fluctuations from a site of interest inside the biological body to a transducer located outside the biological body. An inherent disadvantage of such a system is the possibility of blood clots forming in the catheter, which, if released in the body, could harm the subject. Also, any clot formation tends to occlude the catheter lumen resulting in dampened and distorted pressure waves which lead to erroneous or difficult to interpret signals from the transducer. These potential problems are usually controlled by intermittently or continuously flushing the catheter with an anti-coagulant fluid. The flushing itself can cause problems by dislodging and discharging into the biological body an already formed clot. Additionally, a bolus of air could accidently be introduced with the flushing liquid which could have a detrimental effect on the biological body. Further, the amount of flushing permissible is limited by the biological body's tolerance to the flushing liquid. Other disadvantages of external transducer systems are the possibility of erroneous blood pressure measurements caused by a difference in elevation of the external sensor and the site of pressure measurement in the body and by artifacts superimposed on the signal of interest caused by movement of the catheter, sometimes known as catheter whip, distortion of the lumen of the catheter and by movement of the subject.

Another type of commonly used internal blood pressure measuring transducer is mounted in the catheter itself, usually at the distal end thereof. The catheter is inserted into the subject and is positioned at a site of interest. Since there is no liquid filled column, the afore-described disadvantages and potential dangers of an external transducer system are eliminated. Further, the superior quality of signals from an invasive transducer permits very accurate determinations of the location and extent of such problems as heart valve malformations and malfunctions. The major disadvantages of presently available invasive pressure measurement transducers are their high cost of manufacture and relative fragility.

Examples of such presently known biological transducers can be found in U.S. Pat. No. 3,550,583 to Chiku, U.S. Pat. No. 3,088,323 to Welkowitz, U.S. Pat. No. 4,342,231 to Yamamoto, U.S. Pat. No. 3,710,781 to Huthcins, U.S. Pat. Nos. 3,724,274 and 3,748,623 to Millar, U.S. Pat. No. 4,023,562 to Hynecek, U.S. Pat. No. 4,191,193 to Seo, and U.S. Pat. No. 4,274,423 to Mizuno. Several of these patents show use of temperature compensation features so that the ultimate pressure readings are not subjected to inaccuracies because of temperature variations. However, none show or suggest the employment of the elements thereof to selectively make not only pressure compensated temperature readings but also biological temperatures in the near vicinity of the transducer which are highly desirable in certain medical circumstances.

The present invention overcomes the shortcomings of the prior art by providing a relatively inexpensive and reliable transducer capable of miniaturization for use in biomedical applications which also permits measurement of biological temperatures as well as pressures compensated for temperature variations.

Outside the biomedical arts U.S. Pat. No. 3,968,466 to Nakamura, U.S. Pat. No. 4,085,620 to Tanaka, U.S. Pat. No. 4,222,277 to Kurtz, and U.S. Pat. No. 4,320,664 to Rhen show the use of crystals with multiple strain sensors or pick-ups. However, none of the references show or suggest the use of their crystals to measure biological temperature in addition to pressure and none show or suggest the use of a U-shaped crystal configuration as is taught by the invention and as will be fully described.

In numerous prior art devices separate piezoresistive crystals are employed to provide temperature compensated pressure readings. This requires handling of more than one crystal and exacting mounting, both difficult in extremely small devices. Also, the crystals must be closely matched as to their resistive characteristics to assure accuracy. The present invention overcomes these problems by employing a U-shaped crystal that is configured to provide two inherently matched sensors.

U-shaped crystals are presently used as single sensor elements when a particular length crystal is desired and would be too long for a chosen enclosure. The U-shaped shape is exploited to get the desired length in a minimum space but such crystal configurations are used as a single sensing element in contrast to the present invention wherein a single U-shaped crystal is employed to provide dual and independent sensing elements.

The use of U-shaped crystals is also known in piezo vibrator applications such as in U.S. Pat. No. 2,081,405 to Mason and U.S. Pat. No. 3,683,213 to Staudte. Further, U.S. Pat. No. 3,745,385 to Nakajima, U.S. Pat. No. 4,166,269 to Stephens, and U.S. Pat. No. 4,327,350 to Erichsen show use of notched piezo crystals either for use with conventional sensors or in microresonator applications as in Staudte and Mason.

Means for effecting transmission of forces to crystals are shown in U.S. Pat. No. 3,245,264 to Kaplan and U.S. Pat. No. 4,357,834 to Kimura.

SUMMARY OF THE INVENTION

Therefore, a primary object of the present invention is to provide a pressure and temperature sensor which is ideally suited for the miniaturization necessary for biomedical applications.

A further object of the present invention is to provide a pressure and temperature sensor which can be inserted in a biological body by means of a catheter.

A still further object of the present invention is to provide a pressure and temperature sensor wherein the pressure readings provided are compensated for temperature variations.

Still another object of the present invention is to provide a pressure and temperature sensor which provides not only temperature compensated pressure readings but also biological temperature readings.

Still another further object of the present invention is to provide a pressure and temperature sensor which employs a specially configured gauge element that allows for one piece handling during construction and avoids the need for close matching of diverse crystals.

Another further object of the present invention is to provide a gauge element for use in a pressure and temperature sensor which greatly simplifies assembly.

An additional object of the present invention is to provide a pressure and temperature sensor which includes a gauge element that is simple in design, relatively inexpensive to manufacture, rugged in construction, and efficient in operation.

These objects, as well as further objects and advantages of the present invention will become readily apparent after reading the ensuing description of a non-limiting illustrative embodiment and viewing the accompanying drawings.

A pressure and temperature sensor, according to the principles of the present invention, comprises a first piezoresistive element; a second piezoresistive element; pressure imparting means for imparting pressures to be measured to one of the first and second piezoresistive elements; resistor means exhibiting a predetermined value of resistance; first means for sensing resistance exhibited by the first and second piezoresistive elements and providing a temperature independent output corresponding to the pressure to be measured; and second means for sensing resistance exhibited by the one of the first and second piezoresistive elements not having the pressures imparted thereto, and the resistor means, said second means providing on output independent of the pressures and corresponding to biological temperatures. The first and second piezoresistive elements are preferably interconnected and take the form of a unitary substantially U-shaped member formed of a single site of a silicon crystal.

A sensor for sensing phenomena such as, for instance, pressure and temperature, according to the principles of the present invention comprises a piezoresistive element taking the form of a substantially U-shaped memeber defining two interconnected legs, electrode means being connected to each of said legs and the interconnection therebetween.

BRIEF DESCRIPTION OF THE DRAWINGS

In order that the present invention may be more fully understood it will now be described, by way of example, with reference to the accompanying drawing in which:

FIG. 1 is an end view of one embodiment of the present invention;

FIG. 2 is a cross-sectional view of the embodiment of FIG. 1 taken along the lines 2—2 of FIG. 1;

FIG. 4 is a pictorial representation, in perspective, of another embodiment of the present invention;

FIG. 5 is an enlarged fragmentary partially broken away view of the embodiment of FIG. 4.

DESCRIPTION OF THE PREFERRED EMBODIMENT

Figure 3:
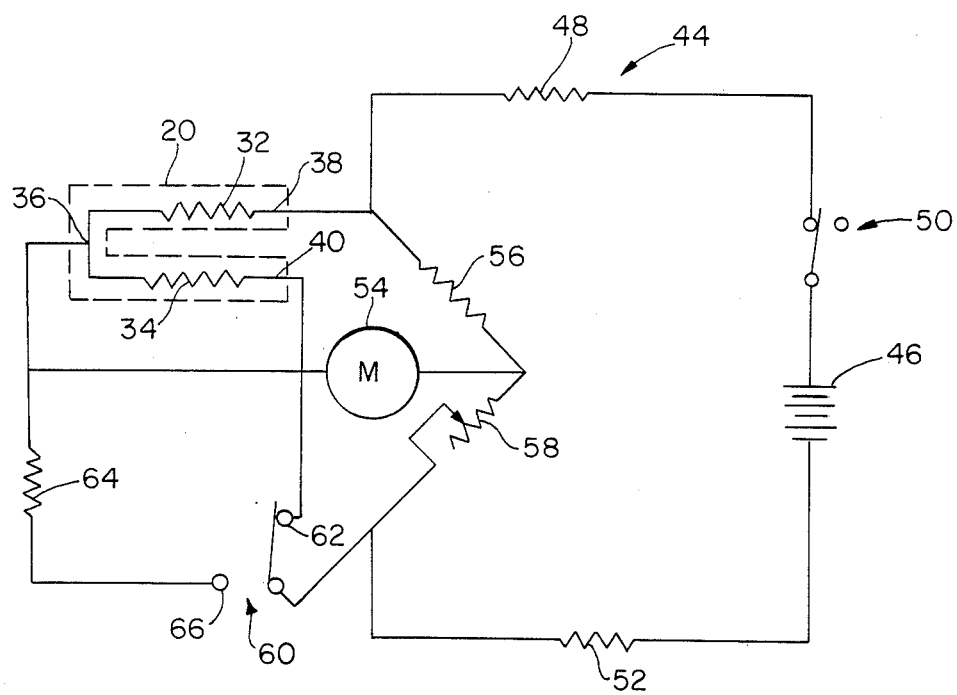
FIG. 3 is the electrical circuit employed in the present invention.

Referring now to the figures, and more particularly to FIGS. 1 and 2 thereof, there is illustrated therein a pressure and temperature sensor 10 which incorporate the principles of the present invention. The pressure and temperature sensor 10 includes an elongated housing 12, preferably constructed of stainless steel or a like suitable material. Elongated housing 12 has an opening 14 at one end thereof in which is mounted a sensor mounting ring 16, preferably constructed of fused quartz or a similar dimensionally stable material. The sensor mounting ring 16 is secured in the opening 14 by a epoxy fillet 18, although other suitable affixing means could be employed.

The sensor mounting ring 16 serves to mount the sensor gauge element 20 which will hereinafter be described in detail. The sensor mounting ring 16 has an opening 22 over which is sealed a flexible diaphragm constructed of surgical grade silicone rubber or the like. Positioned between the interior of the flexible diaphragm 24 and the sensor gauge element 20 is a force summing plate 26 and a shaft 28. The force summing plate 26 and the shaft 28 can be held in position in any suitable and conventional manner and for instance the force summing plate can be finally secured to the flexible diaphragm 24 and the shaft 28 can be fixedly secured to the force summing plate 26.

As can best be seen in FIG. 1, the pressure gauge element 20 is substantially U-shaped and includes a median or bight portion 30 and leg portions 32 and 34. The sensor gauge element 20 is of the piezoresistive type and is constructed such as to form a monolithic bifurcated silicon strain gauge and is cut from a single site of a doped silicon crystal. An electrical contact 36 is disposed on the sensor gauge element 20 at the bight portion 30 thereof, an electrical contact 38 is disposed on the sensor gauge element 20 at the end of the leg portion 32 thereof, and an electrical contact 40 is disposed on the sensor gauge element 20 at the end of the leg 34 thereof. These electrical contacts 36 through 40 are coupled to a circuit which will be hereinafter described in conjunction with the illustration of FIG. 3.

The sensor gauge element 20 is mounted in a conventional manner on the sensor mounting ring 16 and is positioned so that only the leg portion 34 thereof is in contact with the shaft 28. As a result, when pressure acts upon the flexible diaphragm 24, this force is imparted to the leg portion 34 of the sensor gauge element 20. The other leg portion 32 of the sensor element 20 is not exposed to any pressure except for the ambient environmental pressure within the housing 12. Insulated electrical leads are connected to the electrical contacts 36, 38, and 40 and are joined in a cable 42 for connection to the circuit shown in FIG. 3.

As a result of the fabrication of the piezoresistive sensor gauge element 20 from a single site of a doped silicon crystal, close matching of the effectively two created sensors, leg portions 32 and 34 is possible without the necessity of extensive testing, selection, and matching of individually fabricated sensors. Furthermore, the necessity of handling more than one crystal during fabrication is eliminated, a particularly important cost saving feature when employed in a miniature apparatus such as in necessary for biomedical applications. In addition, precise placement of more than one sensor gauge element is eliminated because the sensor elements are jointly formed in the fashion aforedescribed and a compact configuration is further provided as a result of the U-shape of the sensor gauge element 20.

As will now be described, the leg portions 32 and 34 of the sensor gauge element 20 are connected in an electrical circuit 44, as illustrated in FIG. 3 such that the leg portion 32 serves as a biological temperature sensor of tissue in the adjacent environment or a temperature compensator and the leg portion 34 serves as a pressure sensor, compensated for temperature variations. With specific reference to FIG. 3, the electrical circuit 44 is seen to comprise an essentially conventional Wheatstone bridge that includes an excitation supply 46 connected on one end thereof to a current limiting resistor 48 through an on/off switch 50 and on the other end thereof to another current limiting resistor 52.

Also included in the Wheatstone bridge is a bridge output indicating meter 54, for example a millivolt meter, and a fixed bridge balancing resistor 56 and a variable bridge balancing resistor 58. The junction of the fixed bridge balancing resistor 56 and the variable bridge resistor 58 is connected to one side of the bridge output indicating meter 54, the other side of the bridge output indicating meter 54 being connected to electrical contact 36 disposed on the bight portion 30 of the sensor gauge element 20. The current limiting resistor 48 is connected on the end thereof, not connected to the switch 50, to the junction of the fixed bridge balancing resistor 56 and the electrical contact 38 disposed at the end of the leg portion 32 of the sensor gauge element 20. The end of the current limiting resistor 52, not connected to the excitation supply 46, is connected to the bight portion of the variable bridge balancing resistor 58 and the wiper of a double throw-single pole switch 60. One pole 62 of the switch 60 is electrically connected to the electrical contact 40 disposed on the leg portion 34 of the sensor gauge element 20. A fixed resistance 64 is connected between the other pole 66 of the switch 60 and the electrical contact 36 disposed at the bight portion 30 of the sensor gauge element 20.

It should be readily apparent therefore that a conventional Wheatstone bridge is provided with the exception of interchangeability between the sensor formed by the leg portion 34 of the sensor gauge element 20 and the fixed resistor 64. The bridge balancing resistor 58 is of the variable type, commonly called a potentiometer, to permit calibration.

When the wiper of the switch 60 is in position as illustrated in FIG. 3, contacting pole 62, the leg portion 34 of the sensor gauge element 20 is in the Wheatstone bridge and the output readable on the bridge output indicating meter 54 is indicative of the pressure imparted to the leg portion 34 but is compensated for changes in temperature by virtue of the inclusion of leg portion 32 in the bridge circuit 44. When the wiper of the switch 60 is positioned to be in contact with pole 66, then the fixed resistance 64, selected to be of a suitable value, is placed in the Wheatstone bridge circuit 44 and the output indicated on the bridge output indicating meter 54 is indicative of the ambient environmental temperature of the surroundings of the housing 12 as sensed by the leg portion 32 of the sensor gauge element 20. As a result, an apparatus is provided which will not only provide the user with pressure readings compensated for temperature variations but which also will selectively give readings of environmental temperature uneffected by the effects of the pressure to be measured. Selection of the values of the current limiting resistors 48 and 52 and the fixed bridge balancing resistor 56 as well as the fixed resistor 64 depend upon the specifications of the bridge output reading meter 54 and the excitation supply 46 as well as the resistive characteristics of the sensor gauge element 20 and are well within the skill of one of ordinary skill in the art. It is contemplated that the switch 60 as well as the excitation supply 46 will be located at some location outside the elongated housing 12, preferably external to the biological body in which the pressure and temperature 10 is placed. However, it is to be understood that other configurations within the principles and scope of the invention are possible.

FIG. 4 illustrates an alternate embodiment of the subject invention, a pressure and temperature sensor 10'. Pressure and temperature sensor 10' includes an elongated housing 12', an opening 14' being disposed in a lateral elongated surface thereof. The opening 14' has mounted therein a flexible diaphragm 24'. The sensor 10' behaves essentially as the sensor 10 with the only difference being the mechanical location of the flexible diaphragm and the necessary internal differences within the housing 12'. With reference to FIG. 5, a fragmentary portion of the sensor 10' can be seen to include a sensor mounting ring 16' and a sensor gauge element 20'. The sensor gauge element 20' includes a bight portion 30' and leg portions 32' and 34', bight portion 34' being acted upon by a force summing plate 26' via a shaft 28' in essentially the same manner that the leg portion 34 of the sensor gauge element 20 is acted upon by the force summing plate 26 and shaft 28. An electrical contact 36' is provided at the bight portion 30' of the sensor gauge element 20' and electrical contacts 38' and 40' are provided, respectively, at the ends of the leg portions 32' and 34' of the sensor gauge element 20'. The electrical contact 30' is electrically connected to a wire 68, the electrical contact 38' is electrically connected to a wire 70, and the electrical contact 40' is electrically connected to a wire 72, wires 68, 70, and 72 all passing, in insulated fashion, through a cable 42'. Aside from the different mechanical arrangement of the sensor gauge element 20' to the housing 12', electrically the sensor gauge element 20' functions exactly as the sensor gauge element 20 in conjunction with a circuit substantially the same as illustrated in FIG. 3. It is of course to be understood that the principles of the present invention can be employed in housings shaped other than the shapes of housings 12 and 12' and the subject invention may be incorporated in other broader application apparatus within the principles and scope of the invention.

It will be understood that various changes in the details, materials, arrangements of parts and operational conditions which have been here indescribed and illustrated in order to explain the nature of the invention may be made by those skilled in the art within the principles and scope of the invention.

Having thus set forth the nature of the invention, what is claimed is:

1. A pressure and temperature sensor comprising:
   a piezoresistive element having first and second legs electrically interconnected at one end thereof;
   pressure imparting means for imparting pressures to be measured to only said first leg;
   resistor means exhibiting a predetermined value of resistance;
   first means for sensing resistance exhibited by said first and second legs of said piezoresistive element such that temperature variations in said first leg are compensated by corresponding temperature variations in said second leg to thereby provide an inherently temperature independent output signal corresponding to said pressure to be measured; and
   second means for sensing resistance exhibited by said second leg and said resistor means, said second means for providing a pressure independent output signal corresponding to environmental temperature.

2. A pressure and temperature sensor in accordance with claim 1, wherein said piezoresistive element takes the form of a unitary substantially U-shaped member formed of a single site of a silicon crystal.

3. A pressure and temperature sensor in accordance with claim 1, wherein said first means and said second means include a Wheatstone bridge configuration.

4. A pressure and temperature sensor in accordance with claim 3, wherein said Wheatstone bridge configuration includes first and second legs having resistors of preselected values, said first means for coupling said first and second legs of said piezoresistive element to said Wheatstone bridge configuration as the third and fourth legs thereof.

5. A pressure and temperature sensor in accordance with claim 4, wherein said Wheatstone bridge configuration includes first and second legs having resistors of preselected values, said second means for coupling said second leg and said resistor means to said Wheatstone bridge configuration as the third and fourth legs thereof.

6. A pressure and temperature sensor in accordance with claim 3, wherein said Wheatstone bridge configuration includes first and second legs having resistors of preselected values, said second means for coupling said second leg and said resistor means to said Wheatstone bridge configuration as the third and fourth legs thereof.

7. A pressure and temperature sensor in accordance with claim 1, additionally comprising a housing, said piezoresistive element and said pressure imparting means being disposed in said housing, and a resilient diaphragm being mounted in an opening in said housing.

8. A pressure and temperature sensor in accordance with claim 7, wherein said housing is elongated to facilitate insertion into a body via a transcutaneous catheter.

9. A pressure and temperature sensor in accordance with claim 8, wherein said opening is disposed in an end of said housing.

10. A pressure and temperature sensor in accordance with claim 8, wherein said opening is disposed in an elongated surface of said housing.

11. A pressure and temperature sensor in accordance with claim 1, wherein said pressure imparting means comprises a flexible diaphragm a force summing plate disposed adjacent to said flexible diaphragm, and a shaft interposed between said force summing plate and said first leg, inward deflection of said flexible diaphragm causing an exertion of force on said first leg.

12. A pressure and temperature sensor comprising:
a first piezoresistive element;
a second piezoresistive element electrically connected to said first piezoresistive element;
pressure imparting means for imparting pressure to be measured to only said first piezoresistive element;
resistor means exhibiting a predetermined value of resistance;
first means for sensing resistance exhibited by said first and second piezoresistive elements such that temperature variations in said first element are compensated by corresponding temperature variations in said second leg to thereby provide an inherently temperature independent output signal corresponding to said pressure to be measured; and
second means for sensing resistance exhibited by said second element and said resistor means, said second means providing a pressure independent output signal corresponding to environmental temperatures.

13. A pressure and temperature sensor in accordance with claim 12, wherein said first and second piezoresistive elements are formed as a unitary structure.

14. A pressure and temperature sensor in accordance with claim 13, wherein said unitary structure is substantially U-shaped.

15. A pressure and temperature sensor in accordance with claim 14, wherein said unitary structure is formed of a single site of a silicone crystal.

* * * * *